(12) United States Patent
Chapman et al.

(10) Patent No.: US 6,562,985 B2
(45) Date of Patent: May 13, 2003

(54) GEMINAL-DINITRO-1-5 DIAZOCINE DERIVATIVES

(75) Inventors: Robert Dale Chapman, Ridgecrest, CA (US); Theodore Axenrod, Englewood Cliffs, NJ (US); Jianguang Sun, Elmhurst, NY (US); Xiao-Pei Guan, Malden, MA (US); Lida Qi, Leonia, NJ (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 10/166,278

(22) Filed: Jun. 3, 2002

(65) Prior Publication Data

US 2002/0161248 A1 Oct. 31, 2002

Related U.S. Application Data

(62) Division of application No. 09/835,783, filed on Apr. 11, 2001, now Pat. No. 6,417,355.

(51) Int. Cl.$^7$ ..................... C07D 317/00; C07C 311/00
(52) U.S. Cl. ........................................ 549/451; 564/82
(58) Field of Search .............................. 564/82; 549/451

(56) References Cited

PUBLICATIONS

Dorothy A. Cichra, Horst G. Adolph, Synthesis of Polynitro– and Nitronitrosoperhydro–1,5–diazocines, Apr. 18, 1983, 4 pp.

R. S. Miller, Research on New Energetic Materials, Mat. Res. Symp. Proc. vol. 418, 1996, 12 pp., 3–14.

Robert D. Chapman, Mark F. Welker, & Charles B. Kreutzberger, Difuoramination of Heterocyclic Ketones: Control of Microbasicity, American Chemical Society, 1998, 5 pp.

Robert D. Chapman, Richard D. Gilardi, Mark F. Welker, & Charles B. Kreutzberger, Nitrolysis of a Highly Deactivated Amide by Protonitronium Synthesis and Structure of HNFX[1], American Chemical Society, 1999, 6 pp.

George A. Olah, Alexander Orlinkov, Alexandros B. Oxyzoglou, & G. K. Surya Prakash, Nitration of Strongly Deactivated Aromatics with Superacidic Mixed Nitric—Triflatoboric Acid ($HNO_3/2CF_3SO_3H–B(O_3SCF_3)_3$),[1a] American Chemical Society, 1995, 3 pp.

*Primary Examiner*—Bruck Kifle
(74) *Attorney, Agent, or Firm*—Anthony J. Serventi; Laura R. Foster

(57) ABSTRACT

This invention involves a new class of compounds, certain geminal-dinitro-substituted heterocycles, including geminal-bis(difluoramino)-substituted heterocyclic nitramines and the production thereof. More specifically, this invention involves the production of 3,3-bis(difluoramino) octahydro-1,5,7,7-tetranitro-1,5-diazocine (TNFX), which may be formulated into explosives and propellant oxidizers. The method of making a 3,3-bis(difluoramino)octahydro-1, 5,7,7-tetranitro-1,5-diazocine comprises reacting a hexahydro-7,7-dinitro-1,5-bis(nitrobenzenesulfonyl)-1,5-diazocin-3(2 H)-one with a difluoramine source to produce a 3,3-bis(difluoramino)octahydro-7,7-dinitro-1,5-bis (nitrobenzenesulfonyl)-1,5-diazocine and reacting said 3,3-bis(difluoramino)octahydro-7,7-dinitro-1,5-bis (nitrobenzenesulfonyl)-1,5-diazocine with a highly reactive nitrating reagent in the presence of a strong Lewis acid, such as antimony pentafluoride, boron triflate or boron fluorosulfonate.

6 Claims, 2 Drawing Sheets

GEMINAL-DINITRO-1-5 DIAZOCINE DERIVATIVES

CROSS-REFERENCE TO RELATED APPLICATIONS

This application is being filed as a Divisional Application in accordance with 37 C.F.R. 1.53(b). The Parent Application of this Divisional Application is application Ser. No. 09/835,783 filed Apr. 11, 2001 now U.S. Pat. No. 6,417,355.

BACKGROUND OF THE INVENTION

1. Field of the Invention

This invention involves a new class of compounds, geminal-bis(difluoramino)-substituted heterocyclic nitramines, and the production thereof. More specifically, this invention involves the production of 3,3-bis(difluoramino)octahydro-1,5,7,7-tetranitro-1,5-diazocine (TNFX), which may be formulated into explosives and propellant oxidizers.

2. Description of the Related Art

The synthesis of certain examples of this class of compounds, geminal-bis(difluoramino)-substituted heterocyclic nitramines, is difficult and nonintuitive. The certain examples that are particularly synthetically difficult are molecules that incorporate the geminal-bis(difluoramino) alkylene [C(NF$_2$)$_2$] component and the nitramine component [N—NO$_2$] in close proximity, especially when separated by only a methylene (CH$_2$) link in order to maintain a low fuel-to-oxidizer component ratio and con comitantly high oxygen balance in the product molecule. This invention involves 3,3-bis(difluoramino)octahydro-7,7-dinitro-1,5-diazocine derivatives (a heretofore unknown specific class of compound) and novel precursors to these new derivatives, by the use of certain key intermediates and reagents which allow formation of this target structural subcomponent.

The calculated performance improvements expected from geminal-bis(difluoramino)-substituted heterocyclic nitramines when formulated into explosives and propellants has been reported. [Miller, *Materials Research Society Proceedings* 1996, 418, 3].

Methodology for preparing a geminal-bis(difluoramino)-substituted nitrogenous heterocycle has been reported in Chapman et al. *Journal of Organic Chemistry* 1998, 63, 1566, incorporated herein by reference, who describe the preparation of 3,3,7,7-tetrakis(difluoramino) octahydro -1,5-bis(4-nitrobenzenesulfonyl)-1,5-diazocine; this intermediate was converted to the corresponding nitramine, 3,3,7,7-tetrakis(difluoramino) octahydro-1,5-dinitro-1,5-diazocine, given the acronym HNFX as discussed in Chapman et al, *Journal of Organic Chemistry* 1999, 64, 960, incorporated herein by reference.

Methodology for preparing a structurally similar geminal-dinitro-substituted nitrogenous heterocycle has been reported by Cichra and Adolph [*Synthesis* 1983, 830], who describe the preparation of octahydro-1,3,3,5,7,7-hexanitro-1,5-diazocine.

However, the preparation of asymmetric octahydro -1,5-diazocine derivatives incorporating both geminal-dinitro and geminal-bis(difluoramino) substituents has not been previously described. A particularly attractive target compound in terms of providing this asymmetric functionality would be 3,3-bis(difluoramino)octahydro-1,5,7,7-tetranitro-1,5-diazocine, given by us the acronym TNFX by analogy to the acronyms HNFX and RNFX. The incorporation of both functionalities provides a difluoramino component desired for energetic combustion of metallized-fuel propellant formulations, and the gem-dinitro component provides higher oxygen balance (for more-complete combustion) than analogous all-difluoramino derivatives.

SUMMARY OF THE INVENTION

The present invention relates to 3,3-bis(difluoramino) octahydro-1,5,7,7-tetranitro -1,5-diazocine (TNFX) and precursors leading to TNFX and provides a process for the preparation of TNFX having the formula:

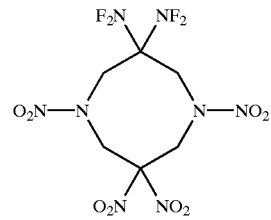

A preferred embodiment of the present invention relates to methods for the preparation of certain new geminal-dinitro-1,5-diazocine derivatives which are suitable precursors leading to TNFX. The invention also involves novel and nonintuitive methods for the preparation of TNFX, a specific member of a general class of compounds with the substructure 3,3-bis(difluoramino)octahydro-7,7-dinitro-1,5-diazocine. TNFX is produced by the use of intermediates which allow formation of the target structural subcomponents, octahydro-3,3-dinitro-1,5-diazocine and a more specific substructure of 3,3-bis(difluoramino) octahydro-7,7-dinitro-1,5-diazocine.

In a preferred embodiment of the present invention, the substitution on heterocyclic precursors' nitrogen atoms is significant. The nitrogen atoms of heterocyclic precursors (such as diazocines) must be suitably substituted, or "protected," during the process of difluoramination to allow this process to proceed to geminal-bis(difluoramino) alkylene derivatives. Without suitable protection of proximate multiple nitrogens, especially those separated from reacting carbonyl sites by a short bridge, such as methylene, the process of difluoramination of ketone intermediates does not proceed to geminal-bis(difluoramino)alkylene derivatives. The result is mono(difluoramino) alkylene derivatives or no reaction at all.

In a preferred embodiment of the present invention, the method of making a 3,3-bis(difluoramino)octahydro -1,5,7, 7-tetranitro-1,5-diazocine comprises reacting a hexahydro-7,7-dinitro-1,5-bis(nitrobenzenesulfonyl)-1,5-diazocin-3 (2H)-one with a difluoramine source to produce a 3,3-bis (difluoramino)octahydro-7,7-dinitro-1,5-bis (nitrobenzenesulfonyl)-1,5-diazocine and reacting said 3,3-bis(difluoramino)octahydro-7,7-dinitro-1,5-bis (nitrobenzenesulfonyl)-1,5-diazocine with a highly reactive nitrating reagent in the presence of a strong Lewis acid, such as antimony pentafluoride, boron triflate or boron fluorosulfonate.

An object of a preferred embodiment of the present invention is to create a novel explosive and propellant oxidizer involving geminal-bis(difluoramino)-substituted heterocyclic nitramines.

Another object of a preferred embodiment of the present invention is to provide a method of producing 3,3-bis (difluoramino)octahydro-1,5,7,7-tetranitro-1,5-diazocine (TNFX).

Yet another objective of object of a preferred embodiment of the present invention is provide a method of producing TFNX in appreciable yield by removing the electron withdrawing nitrobenzene sulfonyl nitrogen protecting groups on 3,3-bis(difluoramino)octahydro-7,7-dinitro-1,5-bis (nitrobenzenesulfonyl)-1,5-diazocine with sufficiently reactive nitrating reagent.

BRIEF DESCRIPTION DRAWINGS

DETAILED DESCRIPTION OF THE INVENTION

The present invention relates to 3,3-bis(difluoramino) octahydro-1,5,7,7-tetranitro-1,5-diazocine (TNFX)and provides a process for the preparation of TNFX having the formula:

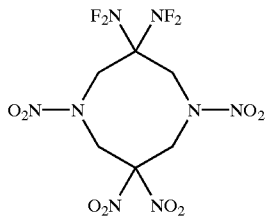

Figure 1:
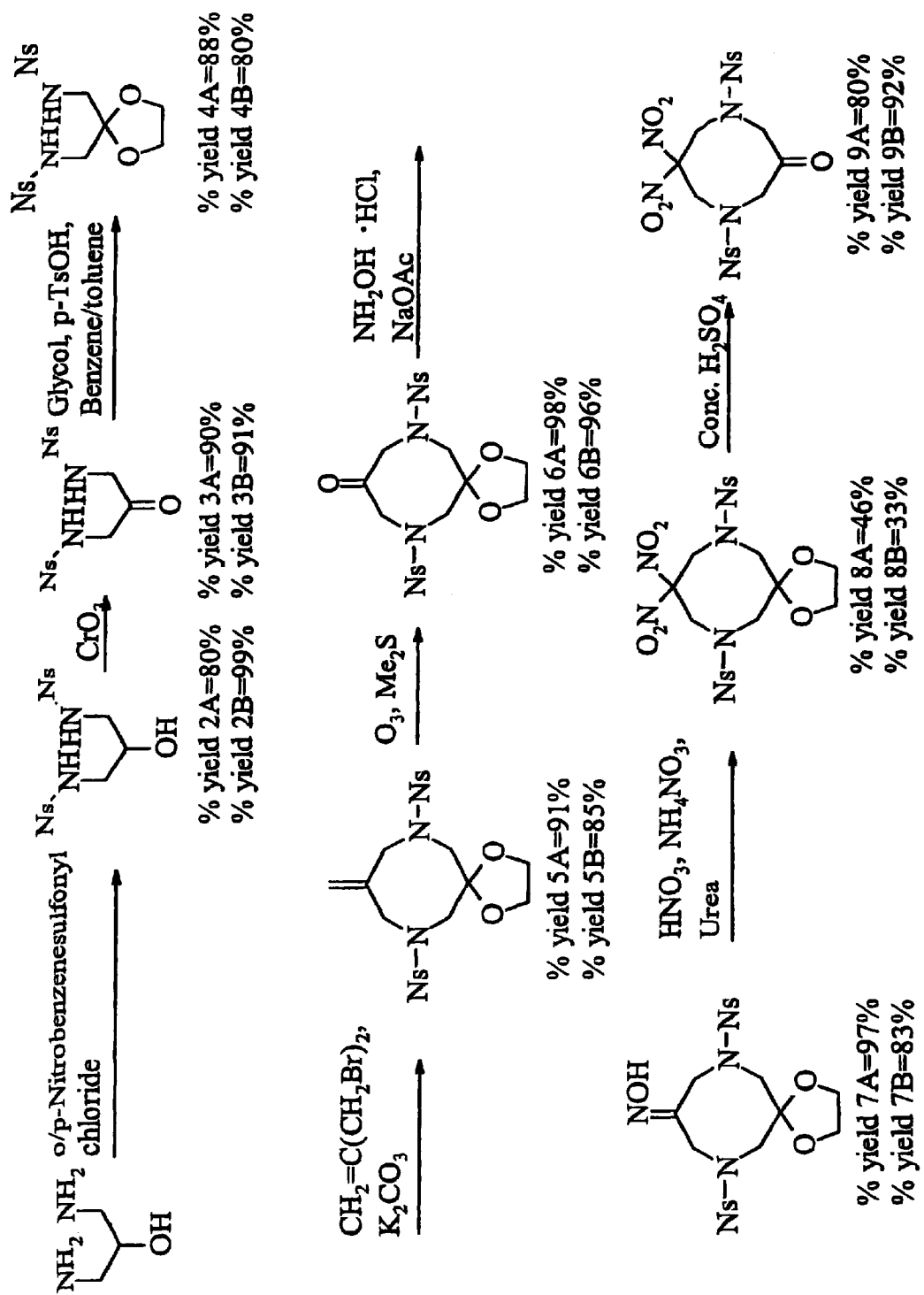
FIG. 1 is a diagram of a general reaction path of a preferred embodiment of the present invention, which details the diazine intermediates.

A preferred embodiment of the process of the present invention utilizes diazocine intermediates, which are suitable for eventual conversion to TNFX. The reaction path of a preferred embodiment of the present invention, generally, is described in FIG. 1. In FIG. 1, the % yield is the experimental % yield of 2A through 9A and 2B through 9B, 2A through 9A represents the experimental results where Ns is o-nosyl

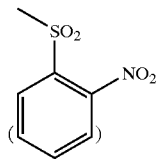

derivative and
2B through 9B represents the experimental results where Ns is p-nosyl

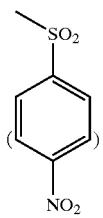

derivative respectively.

In addition to o-nosyl and p-nosyl, the sulfonyl substituents, Ns, may include alkanesulfonyl, halosulfonyl, or arenesulfonyl substituents, but the arenesulfonyl must have electron-withdrawing subsitituents on the phenyl rings. For example, the nitro group ($NO_2$) is a suitable electron-withdrawing subsitituent. Any single or multiple electron-withdrawing subsitituent(s) that collectively lower(s) the basicity of the arenesulfonyl-protected nitrogens below that of the oxygen will be suitable. Similarly, alkanesulfonyl protecting groups may be electronegatively substituted to impart the same property on the protected nitrogens. In general, the sulfonyl substituent must have an inductive substituent constant ($\sigma_1$ or F) of a value greater than that of unsubstituted benzenesulfonyl, approximately 0.58. Examples of preferable sulfonyl substituents are halosulfonyl, any regioisomer of fluoroarenesulfonyl, such as 2-,3- and 4-fluoro-substituted arenesulfonyl, polyhaloalkanesulfonyl, polyhaloarenesulfonyl, any regioisomer of cyanoarenesulfonyl, such as 2-,3- and 4-cyano-substituted arenesulfonyl, polycyanoarenesulfonyl, any regioisomer of nitroarenesulfonyl, such as 2-,3- and 4-nitro-substituted arenesulfonyl and polynitroarenesulfonyl.

Figure 2:
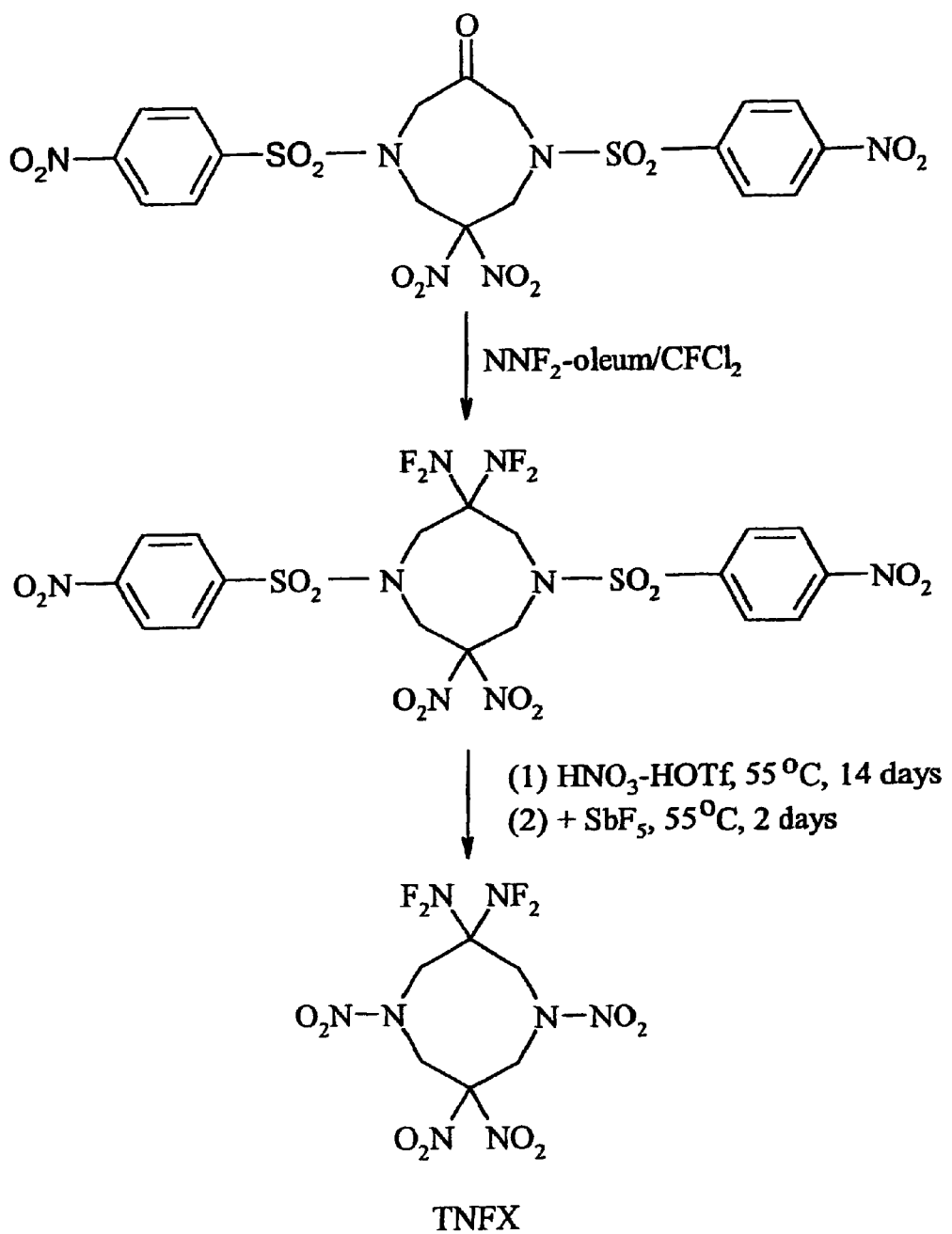
FIG. 2 is a diagram of the a general reaction path of a preferred embodiment of the present invention, which details the steps for conversion of hexahydro-7,7-dinitro-1, 5-bis(2-nitrobenzenesulfonyl)-1,5-diazocin-3(2H)-one to TNFX.

The synthetic sequence leading to TNFX involves substitution on heterocyclic precursors' nitrogen atoms. The nitrogen atoms of heterocyclic precursors (such as diazocines) must be suitably substituted, or "protected," during the process of difluoramination to allow this process to proceed to geminal-bis(difluoramino)alkylene derivatives. Without suitable protection of proximate multiple nitrogens, especially those separated from reacting carbonyl sites by a short bridge, such as methylene, the process of difluoramination of ketone intermediates does not proceed to geminal-bis(difluoramino)alkylene derivatives. A preferred embodiment of the present invention is illustrated in FIG. 2.

In addition to the preferred p-nosyl substituent illustrated above several other sulfonyl subsitituents may be utilized. The sulfonyl substituents may include alkanesulfonyl, halosulfonyl, or arenesulfonyl substituents, but the arenesulfonyl must have electron-withdrawing subsitituents on the phenyl rings. For example, the nitro group ($NO_2$) is a suitable electron-withdrawing subsitituent. Any single or multiple electron-withdrawing subsitituent(s) that collectively lower(s) the basicity of the arenesulfonyl-protected nitrogens below that of the oxygen will be suitable. Similarly, alkanesulfonyl protecting groups may be electronegatively substituted to impart the same property on the protected nitrogens. In general, the sulfonyl substituent must have an inductive substituent constant ($\sigma_1$ or F) of a value greater than that of unsubstituted benzenesulfonyl, approximately 0.58. Examples of preferable sulfonyl substituents are halosulfonyl, any regioisomer of fluoroarenesulfonyl, such as 2-,3- and 4-fluoro-substituted arenesulfonyl, polyhaloalkanesulfonyl, polyhaloarenesulfonyl, any regioisomer of cyanoarenesulfonyl, such as 2-,3- and 4-cyano-substituted arenesulfonyl, polycyanoarenesulfonyl, any regioisomer of nitroarenesulfonyl, such as 2-,3- and 4-nitro-substituted arenesulfonyl and polynitroarenesulfonyl.

The synthetic sequence leading to TNFX is continued from the intermediates detailed in Scheme 1, especially the immediately previous intermediate, hexahydro -7,7-dinitro-1,5-bis(nitrobenzenesulfonyl)-1,5-diazocin-3(2H)-one, by transformations effecting difluoramination of the carbonyl group (i.e., conversion to a gem-bis(difluoramino)alkylene component), which is accomplished by conversion of the ketone carbonyl group in a reaction with difluoramine or difluorosulfamic acid in the presence of a strong acid acid such as sulfuric acid (including fuming sulfuric acid). The subsequent (sequent) nitrolyses of the nitrobenzenesulfonyl N-protecting groups in order to prepare the corresponding bisnitramine, TNFX, as shown in Scheme 2 above.

The latter steps of the sequence (i.e., the N-nitrolyses) are particularly difficult, and the successful conditions leading to nitrolysis to the bisnitramine (TNFX) are particularly novel and nonintuitive, due to the highly deactivating nature of the numerous electron-withdrawing and sterically hindering groups attached to the nitrolyzed nitrogens. The adverse effects of electron-withdrawing and sterically hindering groups on susceptibility of protected nitrogens to N-nitrolysis have been previously reviewed by Chapman et al. *Journal of Organic Chemistry* 1999, 64, 960, incorporated herein by reference. In highly deactivated amides (N-protected amines), such as suitable precursors to HNFX and TNFX, N-nitrolysis requires the use of a highly reactive nitrating reagent such as protonitronium ($NO_2H_2^+$), formed via protonation of a nitronium ($NO_2^+$) source in a very strong acid, i.e., a superacid. The highly reactive nitrating reagent protonitronium ($NO_2H_2^+$) is more efficiently formed in systems combining a superacid with a strong Lewis acid, in order to increase the acidity of the system. The system trifluoromethanesulfonic acid-antimony pentafluoride is used in a preferred embodiment of the present invention. Other examples of superacid systems suitable for formation of protonitronium may utilize other perfluoroalkanesulfonic acids, fluorosulfonic acid, or hydrogen fluoride in the presence of certain Lewis acids. Other Lewis acids which may be suitable for forming protonitronium in combination with superacids include a variety of halides and pseudohalides of main group elements and of certain transition metals such as tantalum. The formation of protonitronium in other superacid systems has been described by Olah et al., *Journal of Organic Chemistry* 1995, 60, 7348, who use the superacid system trifluoromethanesulfonic acid-triflatoboric acid. In the present preparation of TNFX, the cumulative deactivating effects of electronegative and bulky β,β-bis (difluoramino)alkyl and β,β-dinitroalkyl substituents on the diazocine nitro gens (imparting a pseudoneopentyl steric environment to them), and the electron-withdrawing nitrobenzenesulfonyl N-protecting groups, rendered the intermediate 3,3-bis(difluoramino)octahydro -7,7-dinitro-1, 5-bis(nitrobenzenesulfonyl)-1,5-diazocine resistant to nitrolysis even by the strong nitrating system nitric acid-trifluoromethanesulfonic acid, as had been successfully used for previous preparations of HNFX. A modification of the nitrating system was required in order to generate sufficient protonitronium ion (in situ) to effect N-nitrolysis of the nitrobenzenesulfonyl protecting groups and generate the desired TNFX in appreciable yield. Thus, the addition of a strong Lewis acid to the system with nitric acid-trifluoromethanesulfonic acid rendered the nitrating reagent sufficiently reactive to remove both N-protecting groups under appropriate conditions to generate TNFX. In a preferred embodiment of the present invention, the strong Lewis acid antimony pentafluoride is used, but other Lewis acids such as boron triflate or boron fluorosulfonate may be utilized.

Further, the use of para-nitrobenzenesulfonyl-protected diazocines is shown as a preferred embodiment in Scheme 2. The use of ortho-nitrobenzenesulfonyl-protected diazocines produced desired nitramine(s) in only low (though detectable) yield, tentatively due to competing C-nitration at the initially unsubstituted para positions of ortho-nitrobenzenesulfonyl protecting groups. Resultant 2,4-dinitrobenzenesulfonyl protecting groups are subsequently much more difficult to remove than mononitrobenzenesulfonyl protecting groups, and TNFX is formed only to a small extent by successful competition of N-nitrolysis of two ortho-nitrobenzenesulfonyl protecting groups against C-nitration of the para position(s) of protecting groups.

The most desirable product, TNFX, exhibits further attractive attributes in addition to its combination of difluoramino and C-nitro substituents. Samples of TNFX have exhibited the property of crystal polymorphism, as determined by X-ray diffraction analysis. Thus, one polymorph of TNFX shows a higher density than the single crystal form of HNFX that has been observed to date, proving that polymorphism in 3,3,7,7-tetrasubstituted octahydro-1,5-dinitro-1,5-diazocines is a feasible phenomenon to induce, as had been computationally predicted for HNFX though not yet experimentally observed.

EXAMPLES

Example 1

Preparation of hexahydro-7,7-dinitro-1,5-bis(4-nitrobenzenesulfonyl)-1,5-diazocin-3(2H)-one ethylene ketal ("Ns"=p-nitrobenzenesulfonyl)

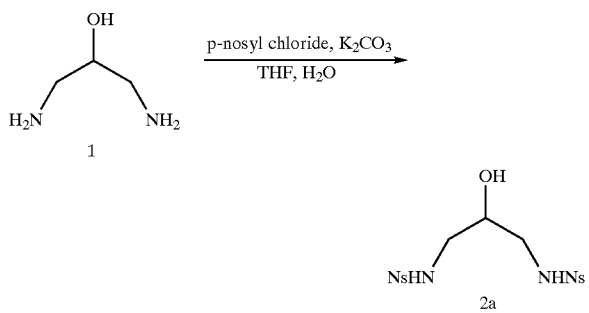

To a stirred solution of 1 (5.30 g, 58.8 mmole) and potassium carbonate (21.54 g, 155.8 mmole) in water (100 mL) maintained at 0° C. was added p-nosyl chloride (29.27 g, 132.1 mmole) in THF (60 mL) dropwise. Upon completion of the addition, the reaction mixture was stirred at room temperature overnight and then concentrated under reduced pressure to remove THF. The solid was filtered. After washed with water, methylene chloride and dried, compound 2a was afforded as a pale yellow solid (25.57 g, 95%); 2a was chromatographed on silica gel eluting with ethyl acetate/hexanes (1:1). Removal of solvent and recrystallization from acetone and hexanes gave a colorless crystalline solid: mp 210–212° C. (sub.). $^1$H NMR (acetone-$d_6$): δ2.96 (m, 2 H), 3.11 (m, 2 H), 3.78 (m, 1 H), 4.40 (d, J=5.49 Hz, 1 H), 6.89 (t, 2 H), 8.11 (d, J=9.16 Hz, 4 H), 8.42 (d, J=9.15, 4 H). $^{13}$C NMR (acetone-$d_6$): δ47.4, 69.8, 125.2, 129.2, 147.5, 151.0. MS (CI/$NH_3$): m/z 478 ($M^+$+1+$NH_3$, 100). Anal. Calcd for $C_{15}H_{16}N_4O_9S_2$: C, 39.13; H, 3.50; N, 12.17. Found: C, 39.46; H, 3.55; N, 11.86.

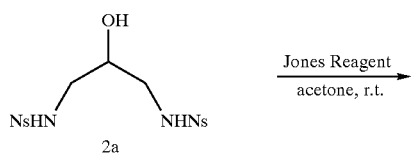

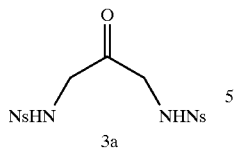

To a stirred solution of 2a (10.28 g, 22.35 mmole) in acetone (300 mL) maintained at 0 20° C. was added dropwise a mixture of $CrO_3$ (5.82 g, 58.2 mmole) in water (15 mL) containing concentrated sulfuric acid (6 mL). After the addition was complete, the reaction mixture was stirred vigorously at room temperature overnight and poured into ice-water. Solid was filtered, washed with water and dried. Compound 3a was obtained as a white solid (9.31 g, 91%), which was recrystallized from acetone and hexanes to give a colorless crystalline solid: mp 212° C. (dec.). $^1$H NMR (acetone-$d_6$): δ4.12 (d, J=5.50 Hz, 4 H), 7.19 (t, 2 H), 8.09 (d, J=9.16 Hz, 4 H), 8.39 (d, J=9.15 Hz, 4 H). $^{13}$C NMR (DMSO-$d_6$): δ49.1, 124.3, 127.9, 146.1, 149.4, 199.9. MS (CI/$NH_3$): m/z 476 ($M^+$+1+$NH_3$,100). Anal. Calcd for $C_{15}H_{14}N_4O_9S_2$: C, 39.30; H, 3.08; N, 12.22. Found: C, 39.23; H, 3.03; N, 11.79.

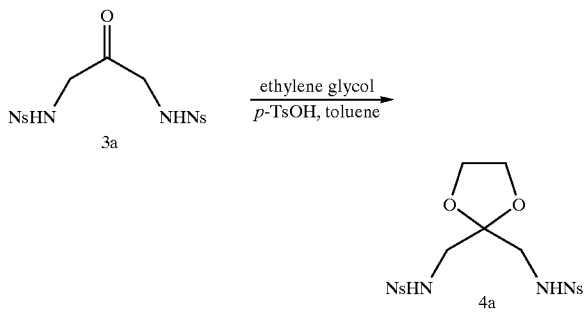

A mixture of ketone 3a (12.29 g, 26.83 mmole), ethylene glycol (6.06 g, 97.63 mmole), and p-toluenesulfonic acid monohydrate (~0.5 g) in toluene (200 mL) was heated under reflux for 3 days using a Dean-Stark apparatus to remove water. After cooling, the solid was filtered, washed with water and methylene chloride. Compound 4a was obtained as a light gray solid (12.12 g, 90%) that was recrystallized from DMF and water to give a colorless crystalline: mp 237° C. (dec). $^1$H NMR (DMSO-$d_6$): δ2.99 (d, J=6.41 Hz, 4 H), 3.59 (s, 4 H), 7.99 (d, J=9.15 Hz, 4 H), 8.13 (t, 2 H), 8.37 (d, J=8.84 Hz, 4 H). $^{13}$C NMR (DMSO-$d_6$): δ45.9, 65.0, 106.7, 124.2, 127.8, 146.7, 149.3. MS (CI/$NH_3$): m/z 520 ($M^+$+1+$NH_3$, 100). Anal. Calcd for $C_{17}H_{18}N_4O_{10}S_2$: C, 40.64; H, 3.61; N, 11.15. Found: C, 40.63; H, 3.44; N, 11.11.

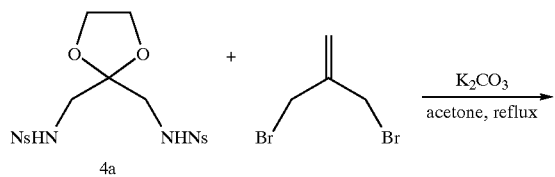

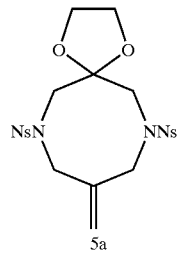

To a refluxed solution of 4a (1.01 g, 2.01 mmole), potassium carbonate (0.72 g, 5.21 mmole) in acetone (50 mL) was added dropwise a solution of 3-bromo-2-(bromomethyl)propene (0.46 g, 2.15 mmole) in acetone (20 mL) in 1 h. The resulting mixture was heated with stirring under reflux overnight and acetone was evaporated. After the residue was washed with water and dried, a yellow solid was afforded which was recrystallized from acetone and hexanes to give 5a as a colorless crystalline solid (0.85 g, 76%): mp 199–201° C. $^1$H NMR ($CDCl_3$): δ3.42 (s, 4 H), 3.81 (s, 4 H), 4.06 (s, 4 H), 5.22 (s, 2 H), 8.04 (d, J=9.16 Hz, 4 H), 8.38 (d, J=9.16 Hz, 4 H). $^{13}$C NMR ($CDCl_3$): δ53.1, 54.0, 65.3, 106.6, 120.9, 124.4, 128.8, 140.0, 144.3, 150.3. MS (CI/$NH_3$): m/z 572 ($M^+$+1+$NH_3$,100). Anal. Calcd for $C_{21}H_{22}N_4O_{10}S_2$: C, 45.48; H, 4.00; N, 10.10; S, 11.56. Found: C, 45.57; H, 4.02; N, 9.65; S, 11.31.

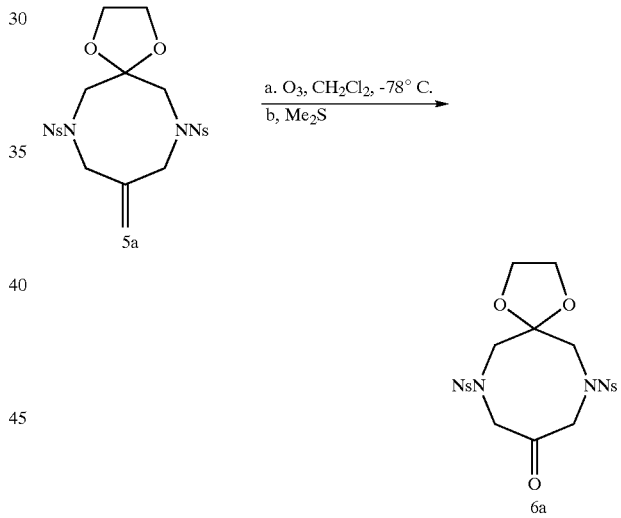

A mixture of ozone in oxygen was bubbled into a stirred solution of 5a (0.98 g, 1.77 mmole) in methylene chloride (100 mL) at −78° C. until the solution turned to blue; then oxygen was continued to bubble into it to remove excess ozone. To the solution was added excess of methyl sulfide. Upon completion of the addition, the mixture was slowly warmed up to room temperature. After stirred for 1 h, solvent was removed under reduced pressure. The residue was washed with water, filtered, washed with water, acetone and dried to afford 6a as a white solid (0.94 g, 95%): mp 244° C. (dec). $^1$H NMR (DMSO-$d_6$): δ3.58 (s, 4 H), 3.92 ( d, J=2.74 Hz, 8 H), 8.10 (d, J=8.24 Hz, 4 H), 8.39 (d, J=9.16 Hz, 4 H). $^{13}$C NMR (DMSO-$d_6$): δ55.1, 64.8, 106.5, 124.7, 128.7, 142.9, 150.1, 202.3. MS (CI/$NH_3$): m/z 574 ($M^+$+1+$NH_3$,100). Anal. Calcd for $C_{20}H_{20}N_4O_{11}S_2$: C, 43.16; H, 3.62; N, 10.07; S, 11.52. Found: C, 42.95; H, 3.60; N, 9.83; S, 11.43.

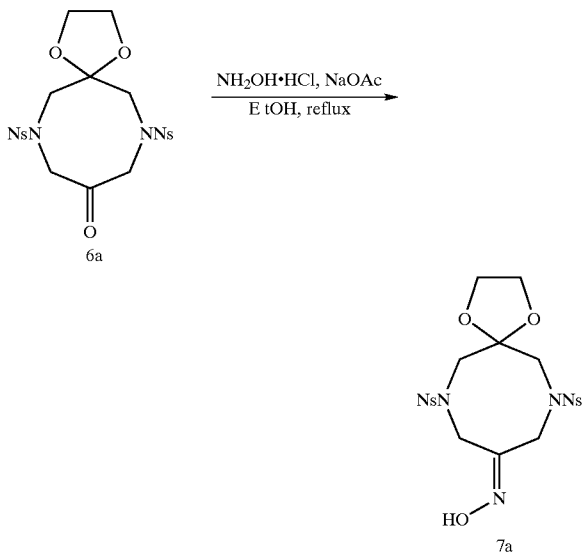

6a

A mixture of 6a (4.00 g, 7.19 mmole), sodium acetate (2.75 g, 33.52 mmole), hydroxylamine hydrochloride (1.02 g, 14.68 mmole) in ethanol (200 mL) was heated with stirring under reflux for 24 h, then cooled to room temperature and poured into ice-water. The precipitate was collected by filtration and dried. A white solid was afforded (3.76 g, 91%) which was recrystallized from acetone and hexanes to give 7a as a colorless crystalline: mp 213° C. $^1$H NMR (DMSO-d$_6$): δ3.30 (s, 2 H), 3.58 (s, 2 H), 3.83 (s, 2 H), 3.84 (s, 2 H), 4.01 (s, 2 H), 4.07 (s, 2 H), 8.08 (dd, J=9.16 Hz, 2.75 Hz, 4 H), 8.38 (m, 4 H),11.3 (s, 1 H). $^{13}$C NMR (DMSO-d$_6$): δ45.0, 50.2, 54.0, 54.3, 64.5, 106.3, 124.3, 124.7, 128.5, 142.8, 144.8, 149.7, 150.0, 152.1. MS (CI/NH$_3$): m/z 589 (M$^+$+1+NH$_3$,100). Anal. Calcd for C$_{20}$H$_{21}$N$_5$O$_{11}$S$_2$: C, 42.03; H, 3.70; N, 12.25; S, 11.22. Found: C, 41.97; H, 3.75; N, 12.12; S, 11.35.

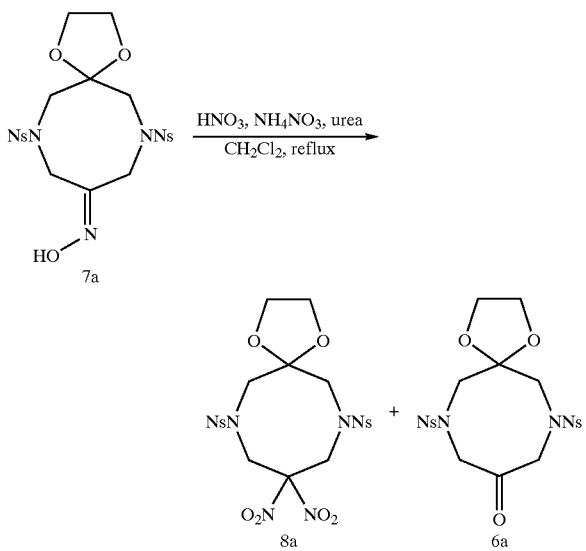

A suspension of 7a (1.75 g, 3.06 mmole) in methylene chloride (100 mL) was heated with stirring under reflux and a solution of 100% nitric acid (15 mL), ammonium nitrate (0.32 g, 4.00 mmole) and urea (0.23 g, 3.83 mmole) in methylene chloride (50 mL) was added dropwise in 1 h. Upon completion of the addition, the reaction mixture was heated under reflux for 1.5 h, cooled to 0° C., and then iced water (150 mL) was added followed by removal of methylene chloride in a vacuum. The resulting mixture was filtered and a pale yellow solid was afforded. The dried solid was stirred in acetone for 20 min and filtered to give a white solid which was identical with compound 6a (0.83 g, 49%). The filtrate was evaporated and the residue was washed with methylene chloride; 8a was afforded as a white solid (0.64 g, 33%) that was recrystallized from acetone and hexanes to give a colorless crystalline: mp 258° C. (dec). $^1$H NMR (DMSO-d$_6$): δ3.45 (s, 4 H), 3.93 (s, 4 H), 4.58 (s, 4 H), 8.09 (d, J=8.24 Hz, 4 H), 8.44 (d, J=9.15 Hz, 4 H). $^{13}$C NMR (DMSO-d$_6$): δ50.2, 55.5, 64.9, 105.7, 118.2, 124.8, 129.1, 141.2, 150.5. MS (CI/NH$_3$): m/z 650 (M$^+$+1+NH$_3$, 100). Anal. Calcd for C$_{20}$H$_{20}$N$_6$O$_{14}$S$_2$: C, 37.98; H, 3.19; N, 13.29. Found: C, 38.19; H, 3.15; N, 12.93.

Example 2

Preparation of hexahydro-7,7-dinitro-1,5-bis(4-nitrobenzenesulfonyl)-1,5-diazocin-3(2H)-one ("Ns"=p-nitrobenzenesulfonyl)

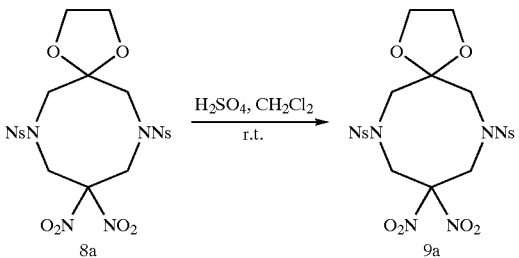

A mixture of 8a (0.64 g, 1.01 mmole) and concentrated sulfuric acid (1 mL) in methylene chloride (20 mL) was stirred at room temperature for 3 days followed by addition of iced water (50 mL). The resulting mixture was filtered and the solid was washed with water, acetone and dried, compound 9a was afforded as a white solid (0.55 g, 92%): mp 230° C. (dec). $^1$H NMR (DMSO-d$_6$): δ4.29 (s, br, 4 H), 4.92 (s, br, 4 H), 8.14 (d, J=8.24 Hz, 4 H), 8.48 (d, J=8.24 Hz, 4 H). $^{13}$C NMR (DMSO-d$_6$): δ54.2, 60.2, 120.3, 125.1, 129.3, 140.4, 150.7, 202.7. MS (CI/NH$_3$): m/z 606 (M$^+$+1+NH$_3$, 25). Anal. Calcd for C$_{18}$H$_{16}$N$_6$O$_{13}$S$_2$: C, 36.74; H, 2.74; N, 14.28. Found: C, 36.80; H, 2.80; N, 13.80.

Example 3

Preparation of 3,3-bis(difluoramino)octahydro-7,7-dinitro-1,5-bis(4-nitrobenzenesulfonyl)-1,5-diazocine In a jacketed tube reactor, 2.0 mL of 30% fuming sulfuric acid plus 10 mL of trichlorofluoromethane were cooled to −25° C., and 2.0 g of difluoramine was condensed into the mixture, which was then warmed to +10° C. (to melt the acid layer) and recooled to −15° C. Solid hexahydro-7,7-dinitro-1,5-bis(4-nitrobenzenesulfonyl)-1,5-diazocin-3(2H)-one (9a, 0.21 g, 0.36 mmol) was added via a solid addition funnel and then washed in with 10 mL trichlorofluoromethane. The mixture was stirred, sealed, at −15° C. for 3 hours and then poured onto ice; the reactor was washed with dichloromethane and then water. The quenched mixture was basified with saturated aqueous sodium bicarbonate to reach a pH of 2, and then extracted with dichloromethane (4×100 mL). The solute was redissolved in hot dichloromethane; chloroform was added; and the mixture was concentrated by rotary evaporation. Precipitate from the dichloromethane-chloroform mixture was filtered off and then redissolved in acetone. The remaining glassware was washed off with acetone, which solution was filtered through a medium-porosity glass frit. Acetone solutions were collected and evaporated to dryness. To the solute was added 25 mL chloroform, 10 mL dichloromethane, and 5 mL acetone, and the mixture was boiled. Dichloromethane was removed by rotary evaporation, and the precipitate was filtered off. The filtered solid as well as the solid residue stuck to the recrystallization flask were dried in a vacuum desiccator. The product was analyzed by NMR to be an acetone adduct of 3,3-bis(difluoramino)octahydro-7,7-dinitro- 1,5-bis(4-nitrobenzenesulfonyl)-1,5-diazocine (0.2358 g); m.p. 208° C. (explodes). $^1$H NMR (acetone-$d_6$): δ2.09 (s), 4.58 (s, br, 4 H), 4.76 (s, 4 H), 8.31 (d, J=9.1 Hz, 4 H), 8.57 (d, J=9.1 Hz, 4 H). $^1$H NMR (DMSO-$d_6$): δ2.09 (s), 4.47 (s, 4 H), 4.59 (s, br, 4 H), 8.19 (d, J=9.0 Hz, 4 H), 8.51 (d, J=9.0 Hz, 4 H). $^{13}$C NMR (DMSO-$d_6$): δ30.7, 49.4, 52.9, 97.8, 118.3, 125.2, 129.9, 140.3, 150.9. $^{19}$F NMR (acetone-$d_6$): δ29.9.

The acetone solvent adduct was dried in a vacuum oven at 50 –55° C. for three days, producing pure bis(difluoramino)octahydro -7,7-dinitro-1,5-bis(4-nitrobenzenesulfonyl)-1,5-diazocine (90% yield). $^1$H NMR (DMSO-$d_6$): δ4.47 (s, 4 H), 4.59 (s, br, 4 H), 8.18 (d, J=8.8 Hz, 4 H), 8.51 (d, J=8.9 Hz, 4 H). $^1$H NMR (CDCl$_3$): δ4.18 (s, br, 4 H), 4.54 (s, 4 H), 8.01 (d, J=9.0 Hz, 4 H), 8.48 (d, J=8.9 Hz, 4 H). $^{19}$F NMR (CDCl$_3$): δ29.3.

Example 4

Preparation of hexahydro-7,7-dinitro-1,5-bis(2-nitrobenzenesulfonyl)-1,5-diazocin-3(2H)-one ethylene ketal ("Ns"=o-nitrobenzenesulfonyl)

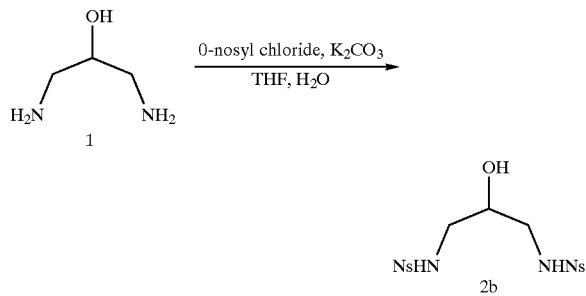

To a stirred solution of 1 (2.38 g, 26.4 mmole) and potassium carbonate (9.35 g, 67.7 mmole) in water (100 mL) maintained at 0° C. was added o-nosyl chloride (11.71 g, 52.8 mmole) in THF (50 mL) dropwise. Upon completion of the addition, the reaction mixture was stirred at room temperature overnight. Layers were separated and the aqueous layer was extracted with ethyl acetate (2×50 ml). The combined organic layers were washed with saturated aqueous sodium bicarbonate and brine and then dried over magnesium sulfate. Removal of solvent gave 2b as a pale yellow solid (9.67 g, 80%). Recrystallization from ethyl acetate and hexanes afforded a white solid: $^1$H NMR (acetone-$d_6$): δ3.08 (m, 2 H), 3.26 (m, 2 H), 3.89 (m, 1 H), 4.56 (d, J=5.49 Hz, 1 H), 6.56 (t, 2 H), 7.92 (m, 6 H), 8.09 (m, 2 H). MS (CI/NH$_3$): m/z 478. Anal. Calcd for C$_{15}$H$_{16}$N$_4$O$_9$S$_2$: C, 39.13; H, 3.50; N, 12.17. Found: C, 38.99; H, 3.49; N, 11.80.

To a stirred solution of 2b (0.48 g, 1.04 mmole) in acetone (20 mL) maintained at 0° C. was added dropwise a mixture of CrO$_3$ (0.30 g, 3.0 mmole) in water (0.63 g) containing concentrated sulfuric acid (0.63 g). After the addition was complete, the reaction mixture was stirred vigorously at room temperature overnight and poured into ice-water. Solid was filtered, washed with water and dried. Compound 3b was obtained as a white solid (0.43 g, 90%), which was recrystallized from acetone and water to give a colorless crystalline solid: mp 165° C. (dec). $^1$H NMR (acetone-$d_6$): δ4.23 (d, J=4.58 Hz, 4 H), 6.90 (t, 2 H), 7.82–8.05 (m, 8 H). MS (CI/NH$_3$): m/z 476. Anal. Calcd for C$_{15}$H$_{14}$N$_4$O$_9$S$_2$: C, 39.30; H, 3.08; N, 12.22. Found: C, 39.25; H, 3.30; N, 12.14.

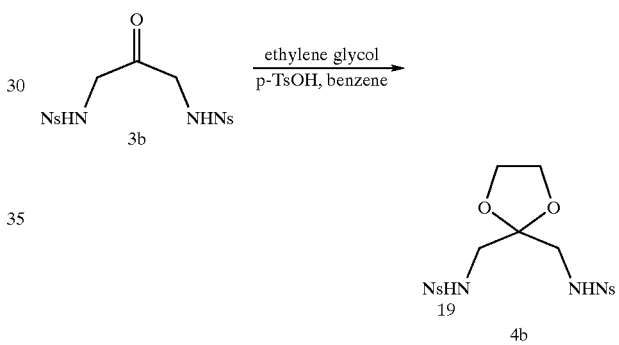

A mixture of ketone 3b (3.30 g, 7.21 mmole), ethylene glycol (1.50 g, 24.17 mmole), and p-toluenesulfonic acid monohydrate (~0.5 g) in benzene (150 mL) was heated under reflux for 3 days using a Dean-Stark apparatus to remove water. After cooling, the solvent was removed and the residue was recrystallized from DMF and water. Compound 4b was obtained as a colorless crystalline (3.20 g, 89%): mp 195–197° C. $^1$H NMR (acetone-$d_6$): δ3.35 (d, J=6.41 Hz, 4 H), 3.69 (s, 4 H), 6.56 (t, 2 H), 7.90 (m, 6 H), 8.05 (m, 2 H). HRMS (FAB): Calc for C$_{17}$H$_{19}$N$_4$O$_{10}$S$_2$ (MH$^+$) 503.0543, found m/z 503.0546. Anal. Calcd for: C$_{17}$H$_{18}$N$_4$O$_{10}$S$_2$ C, 40.64; H, 3.61; N, 11.15. Found: C, 40.67; H, 3.63; N, 11.00.

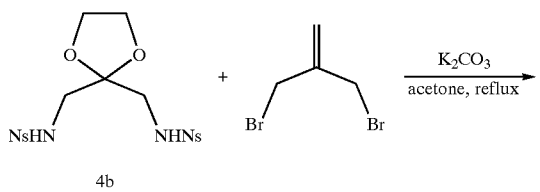

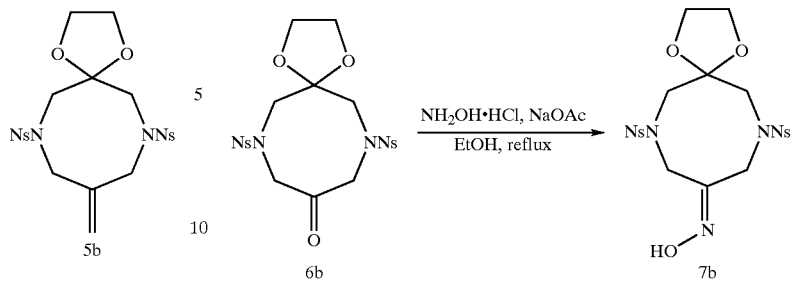

To a refluxed solution of 4b (0.54 g, 1.08 mmole), potassium carbonate (0.43 g, 3.11 mmole) in acetone (50 mL) was added dropwise a solution of 3-bromo-2-(bromomethyl)propene (0.23 g, 1.07 mmole) in acetone (30 mL) in 1 h. The resulting mixture was heated with stirring under reflux overnight and acetone was evaporated. The residue was dissolved in methylene chloride washed with water and dried over magnesium sulfate. Removal of solvent gave a pale yellow solid (0.51 g, 86%). The crude product was purified by passing through silica gel, eluting with ethyl acetate and hexanes, and the resulting solid was recrystallized from ethyl acetate and hexanes, affording a colorless crystalline solid, 5b: mp 150–151° C. $^1$H NMR (CDCl$_3$): δ3.55 (s, 4 H), 4.01 (s, 8 H), 5.26 (s, 2 H), 7.70 (m, 6 H), 8.02 (m, 2 H).

A mixture of 6b (2.14 g, 3.85 mmole), sodium acetate (1.97 g, 24.00 mmole), and hydroxylamine hydrochloride (0.54 g, 7.77 mmole) in ethanol (200 mL) was heated with stirring under reflux for 48 h, and then cooled to room temperature and poured into ice-water. The precipitate was collected by filtration and dried. A white solid was afforded (2.13 g, 97%), which was recrystallized from acetone and hexanes to give 7b as a colorless crystalline solid: mp 220° C. (dec). $^1$H NMR (acetone-d$_6$): δ3.56 (s, 2 H), 3.70 (s, 2 H), 3.97 (s, 4 H), 4.19 (s, 2 H), 4.45 (s, 2 H), 7.92 (m, 6 H), 8.11 (m, 2 H), 10.51 (s, 1 H). HRMS (FAB): Calc for C$_{20}$H$_{22}$N$_5$O$_{11}$S$_2$: (MH$^+$) 572.0757, found m/z 572.0749. Anal. Calcd for C$_{20}$H$_{21}$N$_5$O$_{11}$S$_2$: C, 42.03; H, 3.70; N, 12.25; S, 11.22. Found: C, 42.12; H, 3.91; N, 12.17; S, 11.03.

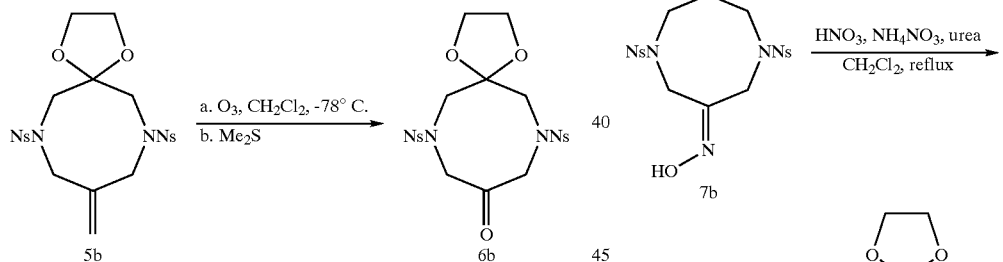

A mixture of ozone in oxygen was bubbled into a stirred solution of 5b (3.26 g, 5.88 mmole) in methylene chloride (250 mL) at −78° C. until the solution turned blue; then oxygen was bubbled into it to remove excess ozone. To the solution was added excess dimethyl sulfide. Upon completion of the addition, the mixture was slowly warmed up to room temperature. After stirring for 1 h, solvent was removed under reduced pressure; 6b was obtained as a white solid (3.20 g, 98%) which was recrystallized from methylene chloride and hexanes to give a colorless crystalline solid: mp 219° C. (dec). $^1$H NMR (DMSO-d$_6$): δ3.67 (s, 4 H), 3.94 (s, 4 H), 4.06 (s, 4 H), 7.90 (m, 4 H), 8.04 (m, 4 H). HRMS (FAB): Calc for C$_{20}$H$_{21}$N$_4$O$_{11}$S$_2$: (MH$^+$) 557.0648, found m/z 557.0652.

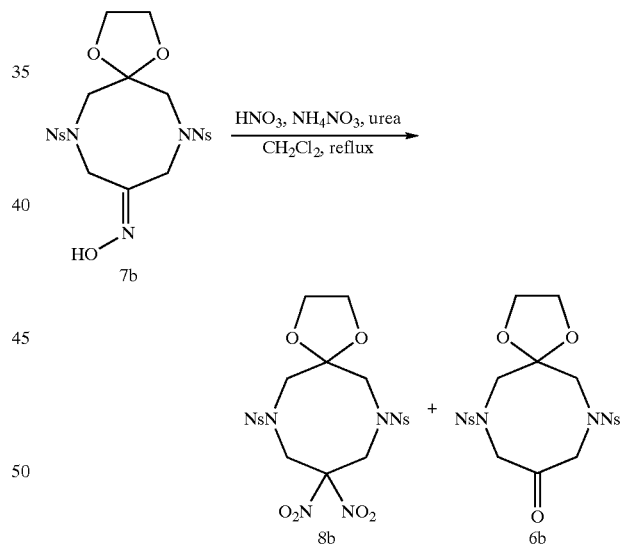

A suspension of 7b (0.39 g, 0.68 mmole) in methylene chloride (30 mL) was heated with stirring under reflux, and a solution of 100% nitric acid (5 mL), ammonium nitrate (81 mg, 0.96 mmole) and urea (82 mg, 1.37 mmole) in methylene chloride (15 mL) was added dropwise over 1 h. Upon completion of the addition, the reaction mixture was heated under reflux for 2 h, cooled to room temperature, washed with water, aqueous sodium bicarbonate, brine and dried over magnesium sulfate. Removal of solvent produced a white solid. The dried solid was stirred in methylene chloride for 20 min and filtered to give 8b as a white solid (0.20 g, 46%), which was recrystallized from DMF and water to afford a colorless crystalline solid: mp 245° C. (dec). $^1$H NMR (DMSO-$d_6$): δ3.57 (s, 4 H), 3.90 (s, 4 H), 4.83 (s, 4 H), 7.87–8.10 (m, 8 H). $^{13}$C NMR (DMSO-$d_6$): δ50.3, 55.3, 64.9, 105.4, 118.2, 124.8, 128.7, 130.0, 132.9, 135.5, 147.9. The filtrate was concentrated; a white solid was obtained which was identical with 6b (0.16 g, 42%).

Example 5

Preparation of hexahydro-7,7-dinitro-1,5-bis(2-nitrobenzenesulfonyl)-1,5-diazocin-3(2H)-one ("Ns"=o-nitrobenzenesulfonyl)

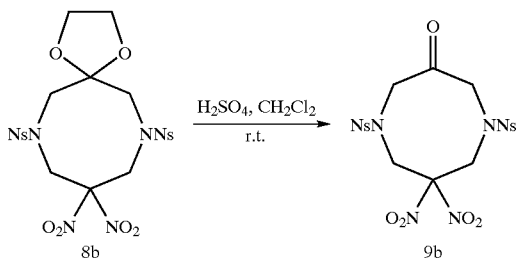

A mixture of 8b (0.80 g, 1.27 mmole) and concentrated sulfuric acid (1 mL) in methylene chloride (20 mL) was stirred at room temperature for 3 days, followed by addition of ice-water (50 mL). The resulting mixture was filtered, and the solid was washed with water and dried; compound 9b was afforded as a white solid (0.65 g, 87%). $^1$H NMR (acetone-$d_6$): δ4.47 (s, 4 H), 5.24 (s, 4 H), 8.06 (m, 8 H). $^{13}$C NMR (DMSO-$d_6$): δ54.9, 60.2, 120.5, 125.7, 128.1, 129.7, 133.6, 136.1, 148.0, 202.6.

Example 6

Preparation of 3,3-bis(difluoramino)octahydro-7,7-dinitro-1,5-bis(2-nitrobenzenesulfonyl)-1,5-diazocine By a procedure similar to that of Example 3, difluoramination of 0.20 g hexahydro-7,7-dinitro-1,5-bis(2-nitrobenzenesulfonyl)-1,5 -diazocin-3(2H)-one (9b) produced 0.1495 g (65% yield) of pure 3,3-bis(difluoramino) octahydro-7,7-dinitro-1,5-bis(2-nitrobenzenesulfonyl)-1,5-diazocine after recrystallization from acetone-chloroform; m.p. 225–228° C. (dec). $^1$H NMR (acetone-$d_6$): δ4.67 (s, br, 4 H), 5.02 (s, 4 H), 8.01–8.21 (m, 8 H). $^{13}$C NMR (acetone-$d_6$): δ50.6 (quintet, J=7.0 Hz), 53.7, 98.0 (m), 118.9, 126.3, 129.5, 132.4, 134.0, 137.3, 149.6. $^{19}$FNMR (acetone -$d_6$): δ629.3.

Example 7

Preparation of 3,3-bis(difluoramino)octahydro-1,5,7,7-dinitro-1,5-diazocine (TNFX)

To 10 mL of triflic acid was added 1.0 mL of 98–100% nitric acid at ambient temperature, and the mixture was stirred for 1 hour. To this mixture cooled in an ice-water bath was slowly added solid 3,3-bis(difluoramino)octahydro-7,7-dinitro-1,5-bis(4-nitrobenzenesulfonyl)-1,5-diazocine (49.6 mg) via a solid addition funnel. The resulting suspension was warmed to 55° C. in an oil bath. After recooling in an ice-water bath, another 1.0 mL nitric acid was added, and the mixture was rewarmed to 55° C. Another 10 mL triflic acid was added dropwise, and the mixture was stirred at 55° C. overnight. Additional triflic acid was added dropwise to make a total of 40 mL of solution, and the solution was stored in an oven at 55° C. After 14 days, one-fourth of the reaction solution was separated, and to this portion was added ~10% by volume of antimony pentafluoride. After two days of storage of this solution at room temperature, most of the triflic acid was vacuum-distilled at 55° C.; the residue was quenched onto ice-water, neutralized to pH 7 with aqueous sodium carbonate, and extracted with dichloromethane. Chromatography of the solute (silica gel, chloroform-dichloromethane) separated 3,3-bis (difluoramino)octahydro-1,5,7,7-dinitro-1,5-diazocine (TNFX) from by-products, and its identity was confirmed by X-ray crystallography. $^1$H NMR (acetone-$d_6$): δ5.14 (s, br, 4 H), 5.50 (s, 4 H). $^{19}$F NMR (acetone-$d_6$): δ29.7.

Although the description above contains many specificities, these should not be construed as limiting the scope of the invention but as merely providing an illustration of the presently preferred embodiment of the invention. Thus the appended claims and their legal equivalents should determine the scope of this invention.

What is claimed is:

1. A compound having the formula

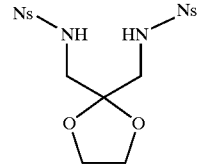

wherein Ns is selected from the group consisting of halosulfonyl, a regioisomer of fluoroarenesulfonyl, polyhaloalkanesulfonyl, polyhaloarenesulfonyl, a regioisomer of cyanoarenesulfonyl, polycyanoarenesulfonyl, a regioisomer of nitroarenesulfonyl, and polynitroarenesulfonyl.

2. The compound of claim 1 wherein said regioisomer of fluoroarenesulfonyl is selected from the group consisting of 2-,3- and 4-fluoro-substituted arenesulfonyl, wherein said regioisomer of cyanoarenesulfonyl is selected from the group consisting of 2-,3- and 4-cyano-substituted arenesulfonyl and wherein said regioisomer of nitroarenesulfonyl is selected from the group consisting of 2-,3- and 4-nitro-substituted arenesulfonyl.

3. A compound having the formula

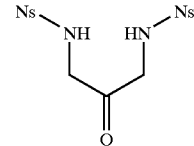

wherein Ns is selected from the group consisting of halosulfonyl, a regioisomer of fluoroarenesulfonyl, polyhaloalkanesulfonyl, polyhaloarenesulfonyl, a regioisomer of cyanoarenesulfonyl, polycyanoarenesulfonyl, a regioisomer of nitroarenesulfonyl, and polynitroarenesulfonyl.

4. The compound of claim 3 wherein said regioisomer of fluoroarenesulfonyl is selected from the group consisting of 2-,3- and 4-fluoro-substituted arenesulfonyl, wherein said regioisomer of cyanoarenesulfonyl is selected from the group consisting of 2-,3- and 4-cyano-substituted arenesulfonyl and wherein said regioisomer of nitroarenesulfonyl is selected from the group consisting of 2-,3- and 4-nitro-substituted arenesulfonyl.

5. A compound having the formula

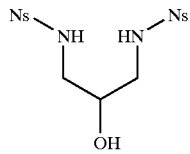

wherein Ns is selected from the group consisting of halosulfonyl, a regioisomer of fluoroarenesulfonyl, polyhaloalkanesulfonyl, polyhaloarenesulfonyl, a regioisomer of cyanoarenesulfonyl, polycyanoarenesulfonyl, a regioisomer of nitroarenesulfonyl, and polynitroarenesulfonyl.

6. The compound of claim 5 wherein said regioisomer of fluoroarenesulfonyl is selected from the group consisting of 2-,3- and 4-fluoro-substituted arenesulfonyl, wherein said regioisomer of cyanoarenesulfonyl is selected from the group consisting of 2-,3- and 4-cyano-substituted arenesulfonyl and wherein said regioisomer of nitroarenesulfonyl is selected from the group consisting of 2-,3- and 4-nitro-substituted arenesulfonyl.

* * * * *